(12) United States Patent
Woods et al.

(10) Patent No.: US 7,323,620 B2
(45) Date of Patent: Jan. 29, 2008

(54) ACTIVATION OF EQUINE OOCYTES

(75) Inventors: Gordon L. Woods, Moscow, ID (US); Dirk K. Vanderwall, Viola, ID (US)

(73) Assignee: Idaho Research Foundation, Inc., Moscow, ID (US)

(*) Notice: Subject to any disclaimer, the term of this patent is extended or adjusted under 35 U.S.C. 154(b) by 659 days.

(21) Appl. No.: 10/411,613

(22) Filed: Apr. 9, 2003

(65) Prior Publication Data

US 2003/0200556 A1  Oct. 23, 2003

Related U.S. Application Data

(60) Provisional application No. 60/374,032, filed on Apr. 18, 2002.

(51) Int. Cl.
| | |
|---|---|
| C12N 15/00 | (2006.01) |
| C12N 5/00 | (2006.01) |
| C12N 5/02 | (2006.01) |
| A01K 67/027 | (2006.01) |
| A61B 5/103 | (2006.01) |
| A61B 5/117 | (2006.01) |

(52) U.S. Cl. .................... 800/24; 800/14; 600/591; 435/325; 435/375

(58) Field of Classification Search .................... None
See application file for complete search history.

(56) References Cited

U.S. PATENT DOCUMENTS

| | | | |
|---|---|---|---|
| 5,471,993 | A | 12/1995 | Yoches |
| 5,496,720 | A | 3/1996 | Susko-Parrish |
| 5,945,577 | A | 8/1999 | Stice |

FOREIGN PATENT DOCUMENTS

| | | |
|---|---|---|
| WO | WO 95/17500 | 6/1995 |

OTHER PUBLICATIONS

Hinrichs, K et al, 1995, Activation of horse oocytes, Biol Reprod Mono, 1:319-324.*
Galli, C et al, Aug. 2003, A clones horse born to its dam twin, Nature, 424:635.*
Woods, GL et al., Aug. 2003, A mule clones from fetal cells by nuclear transfer, Science, 301:1063.*
Li, X et al, 2000, Effects of different activation treatments on fertilization of horse oocytes by intracytoplasmic sperm injection, Journal of Reproduction and Fertility, 119:253-260.*
Boquest, AC, et al., "Production of Cloned Pigs from cultured fetal fibroblast cells", Biology of Reproduction, 66: 1283-1287 (2002).
Bos-Mikich, A, et al., "Meiotic and mitotic Ca+2 oscillations affect cell composition in resulting blastocysts", Developmental Biology, 182:172-179 (1997).
Carneiro, GF, et al., "Quantification and distribution of equine oocyte cortical granules during meiotic maturation and after activation", Molecular Reproduction and Development, 63:451-458 (2002).
Carneiro, G, et al., "Influence of insulin-like growth factor-I and its interaction with gonadotropins, estradiol, and fetal calf serum on in vitro maturation and parthenogenic development in equine oocytes", Biology of Reproduction, 65:899-905 (2001).
Chong, HT, et al., "Effect of elevated Ca+2 concentration in fusion/activation medium on the fusion and development of porcine fetal fibroblast nuclear transfer embryos", Molecular Reproduction and Development, 61:488-492 (2002).
Choi, YH, et al, "Production of Nuclear Transfer Horse embryos by piezo-driven injection of somatic cell nuclei and activation with stallion sperm cytosolic extract", Biology of Reproduction, 67:561-567 (2002).
Choi, YH, et al., "Activation of cumulus-free equine oocytes: effect of maturation medium, calcium ionophore concentration and duration of cycloheximide exposure", Reproduction, 122:177-183 (2001).
Choi, YH, et al., "Effect of co-culture with theca intrean on nuclear maturation of horse oocytes with low meiotic competence, and subsequent fusion and activation rates after nuclear transder", Theriogenology, 57:1005-1011 (2002).
Guignot, F, et al., "Preliminary observations in in vitro development of equine embryo after ICSI", Reprod. Nutr. Dev., 38:653-663 (1998).
Hinrichs, K, et al, "In vitro fertilization of in vitro-matured equine oocytes effect of maturation medium, duration of maturation, and sperm calcium ionophore treatment, and comparison with rates of fertilization in vivo after oviductal transfer", Biology of Reproduction, 67:256-262 (2002).
Inoue, K, et al., "Improved postimplantation development of rabbit nuclear transfer embryos by activation with inositol 1,4,5-trisphosphate", Cloning anf Stem Cells, 4(4):311-317 (2002).
Kato, H., et al., "Treatment of equine oocytes with A23187 after intracytoplasmic sperm injection", Equine Vet. J. Suppl., 25:51-53 (1997).
Kitiyanant, Y, et al., "Somatic Cell cloning in Buffalo (*Bubalus bubalis*): effects of interspecies cytoplasmic recipients and activation procedures", Cloning and Stem Cells, 3(3):97-104 (2001).
Li, X., et al., "In vitro development of horse oocytes reconstructed with the nuclei of fetal and adult cells", Biology of Reproduction, 66:1288-1292 (2002).
Li, X., et al., "influence of co-culture during maturation on the developmental potential of equine oocytes fertilized by intracytoplasmic sperm injection (ICSI)", Reproduction, 121:925-932 (2001).
Squires, EJ, "Maturation and fertilization of equine oocytes", Reproductive Technology, 12(1):31-45 (1996).
Zhang, JJ, et al., "In vitro fertilization of horse follicular oocytes matured in vitro", Molecular Reproduction and Development, 26:361-365 (1990).
Li, et al, "Effects of different activation treatments on fertilization of horse oocytes by intracytoplasmic sperm injection," J. Reprod. and Fertility, 119:253-260 (2000).

* cited by examiner

*Primary Examiner*—Valarie Bertoglio
(74) *Attorney, Agent, or Firm*—Howard Eisenberg, Esq.

(57) ABSTRACT

A method for activating an equine oocyte comprising exposing oocyte to a medium containing a concentration of calcium of at least about 4 mM. Preferably the oocyte is exposed to this concentration of calcium during activation.

20 Claims, 1 Drawing Sheet

ACTIVATION OF EQUINE OOCYTES

This application claims the priority of pending U.S. Provisional Patent Application Serial No. 60/374,032, filed Apr. 18, 2002.

FIELD OF THE INVENTION

The invention pertains to the field of establishing pregnancy by such methods as in-vitro fertilization and nuclear transfer.

BACKGROUND OF THE INVENTION

Cloning by nuclear transfer is performed by fusing a nuclear donor cell with an enucleated oocyte, typically a metaphase II oocyte. The resulting nuclear transfer embryo uses the donor cell DNA as the template for subsequent gene expression, thus producing a genetically identical clone of the donor cell line. Nuclear transfer research has increased our understanding of basic aspects of oocyte physiology and cell biology, and has tremendous potential for practical application in production animal agriculture and for the preservation of endangered species.

Nuclear transfer, like in-vitro fertilization, requires activation of an oocyte. In in-vitro fertilization, the oocyte is activated by entry of sperm into the oocyte. In nuclear transfer, activation is performed parthenogenetically, that is without the use of sperm. Most commonly, activation of the oocyte is obtained by introducing calcium ions into the activation medium, with or without other factors. In mice, exposure to calcium and magnesium ions has been reported to cause activation of oocytes. This procedure, however, has not proven to be effective in all species. For example, the procedure is ineffective in activating bovine oocytes. Susko-Parrish, U.S. Pat. No. 6,077,710. Susko-Parrish disclosed a method to obtain parthenogenetically activated bovine oocytes which included the steps of increasing divalent calcium cations in the oocyte and reducing phosphorylation of cellular proteins in the oocyte. The level of calcium ions in the oocyte is increased, according to the method of Susko-Parrish, by any method that increases intracellular cellular levels of divalent calcium cations, such as by electrical stimulation or addition of ionomycin to the activation medium. Reduction of phosphorylation of cellular proteins is obtained by addition of a serine-threonine kinase inhibitor, such as 6-dimethylaminopurine (DMAP) to the activation medium.

Nuclear transfer has been used successfully to clone offspring from sheep, cattle, goats, pigs, and mice. It is clear that different animals require different conditions in order to establish pregnancy by nuclear transfer. To date, nuclear transfer has been unsuccessful in establishing pregnancy in equine species.

SUMMARY OF THE INVENTION

It has been discovered that by increasing the divalent calcium ion concentration in an activation medium, pregnancies in species of equidae can be established. It has further been discovered that, by exposing equine oocytes to a calcium concentration of at least about 4 mM, such as during activation in an activation medium, pregnancies in equine species can be established. It is further conceived that by exposing oocytes to an increased divalent calcium ion concentration in media prior to and/or after exposure to an activating agent, with or without a concomitant increase in calcium ion concentration in the activation medium, equine pregnancies may be established.

Accordingly, one embodiment of the invention is a method for activating an equine oocyte. According to this embodiment of the invention, an oocyte is exposed to a concentration of divalent calcium ions of at least about 4 mM. This level is about two or more times that which is presently used in the activation of oocytes. Preferably, such exposure occurs in an activation medium during the time when oocytes are exposed to an activating agent.

In another embodiment, the invention is an activated equine oocyte. Preferably, the equine oocyte had been activated by the method of the invention, that is by exposure in a medium to a concentration of divalent calcium ions of at least about 4 mM. The activated oocyte of the invention is suitable for all in-vivo and in-vitro methods for establishing pregnancy in equidae, including nuclear transfer, and in-vitro fertilization, but excluding methods that utilize natural methods of fertilization such as by breeding and artificial insemination.

Preferably, the medium in which the divalent calcium ion concentration is at least about 4 mM is the activation medium itself. However, in accordance with the method of the invention, the oocytes are exposed to a calcium ion concentration of at least 4 mM in any medium during or peripheral to activation. Thus, the calcium ion concentration is at least 4 mM in culture medium in which oocytes are held prior to activation or in culture medium in which oocytes are held following activation.

In another embodiment, the invention is a method for establishing a pregnancy in an equine. According to this embodiment of the invention, an oocyte is incubated in a medium, preferably an activation medium, containing a concentration of divalent calcium ions of at least about 4 mM, and sperm is introduced into the oocyte. This method is suitable for any non-parthenogenetic method for establishing pregnancy, other than by natural breeding and artificial insemination, such as in-vitro fertilization.

Another embodiment of the invention is a method for establishing a pregnancy in an equine by nuclear transfer. According to this embodiment of the invention, an enucleated oocyte is incubated in a medium, preferably in an activation medium, containing a concentration of divalent calcium-ions of at least about 4 mM and the nucleus of a donor cell is fused with the enucleated oocyte.

In another embodiment, the invention is a pregnant equine female in which the embryo or fetus that is within the uterus of the pregnant equine has a genotype identical to that of a donor equine animal. Preferably, the pregnancy within the equine female has been established by activating the oocyte that has developed into the embryo or fetus according to the method of oocyte activation of the invention.

In another embodiment, the invention is an equine embryo or fetus that has a genotype identical to that of a donor equine animal. Preferably, the embryo or fetus has developed from an oocyte that has been activated according to the method of oocyte activation of the invention.

In another embodiment, the invention is a live equine animal that has a genotype identical to that of a donor equine animal. Preferably, the live equine animal has developed from an oocyte that has been activated according to the method of oocyte activation of the invention.

DETAILED DESCRIPTION OF THE INVENTION

Figure 1:
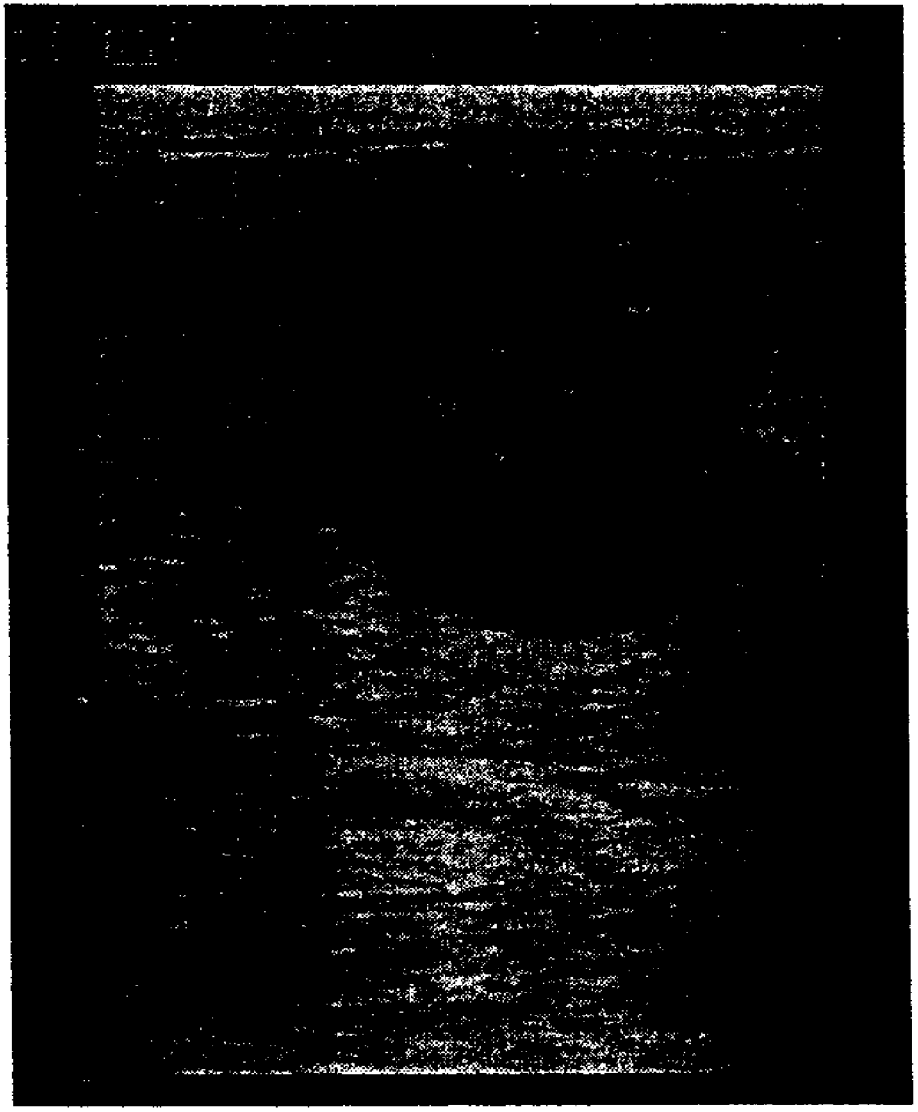
FIG. 1 is an ultrasonogram of a cloned equine conceptus.

According to the preferred method of activation of an equine oocyte, the oocyte is incubated in a medium containing at least about 4 mM divalent calcium ions for a time sufficient to activate the oocyte. Preferably, the medium contains between 4 mM and 200 mM of divalent calcium ions. Most preferably, the concentration of divalent calcium ions in the medium is between 6 and 20 mM. Preferably, the incubation is during activation in an activation medium. Most preferably, peripheral media, that other than the activation medium, also has a calcium concentration of at least about 4 mM. Less preferred, the oocyte is incubated in a medium before and/or after activation in which the concentration of calcium ions is at least 4 mM and the concentration of calcium in the activation medium is less than 4 mM.

Any source of divalent calcium ions is suitable for the invention, so long as the portion of the calcium containing molecule other than $Ca^{2+}$ is not toxic to the oocyte. Preferably, the source of calcium ions is calcium chloride ($CaCl_2$). Other sources of divalent calcium ions are suitable for the method of the invention, such as calcium lactate.

The amount of time that the oocytes should remain in the activation medium is a time sufficient to obtain activation of the oocytes. Activation may be determined by microscopically examining the oocytes at about 12 to 24 hours following removal from the activation medium. If the oocytes have been activated, the oocytes will begin to divide by this time. On the other hand, if there has not been activation, no division will occur. Generally, in the presence of ionomycin, activation by exposure to elevated concentrations of calcium in accordance with the invention typically requires an incubation of a few minutes, such as 4 to 5 minutes or more. In the presence of cyclohexamide, an incubation of several hours, such as 5 hours is typically used. Incubation without either of these agents may require additional time. Regardless of the presence of absence of additional components in the activation medium, the length of time necessary to obtain activation may be determined by observing the presence of cell division.

According to the method of the invention, any method of activation of oocytes, presently known or later discovered, is suitable. For example, activation may be by one or more chemical activation agents, such as an ionophore like ionomycin or A-23187, or by methods such as electroporation. Additionally, kinase inhibitors such as DMAP or cyclohexamide may be utilized in conjunction with or following exposure of oocytes to ionophore. For non-parthenogenetic methods such as in vitro fertilization (IVF), activation of oocytes is by sperm.

According to the preferred method of the invention, the concentration of calcium is at least 4 mM in the activation medium, as described above. Preferably, but not necessarily, at least one and most preferably all of the media in which oocytes or zygotes are held contains calcium in a concentration of at least 4 mM. Thus, it is preferred that medium, such as maturation medium, in which oocytes are incubated prior to activation have a concentration of calcium of at least 4 mM. Likewise, it is preferred that any medium in which activated oocytes are held have a concentration of calcium of at least 4 mM. It is most preferred that all media, both before and after activation, have a calcium concentration of at least 4 mM. It is less preferred, but is in accordance with the method of the invention, that the calcium concentration in the activation medium is less than 4 mM and that the calcium concentration of a medium in which oocytes are held, either or both of before and following activation, is about 4 mM or greater.

Thus, in accordance with the method of the invention, if the concentration of calcium in the activation medium is 4 mM or greater, the calcium concentration of any medium other than that of the activation medium is not critical. If the calcium concentration of the activation medium is 4 mM or greater, then it is only the calcium concentration of this activation medium which is essential for the invention. Thus, a concentration of media in which oocytes are incubated before or after activation may be less than 4 mM.

The source of equine oocytes may be any member of the family of equidae that is capable of producing a viable oocyte. Thus, the source of the oocyte may be an ass, (*Equus asinus*), a Burchell's or Plains zebra (*Equus burchellii*), a domestic horse (*Equus caballus*), a Mongolian wild horse (*Equus caballus przewalskii*), an Asian wild ass (*Equus hemionus*), a Grevy's zebra (*Equus grevyi*), a wild ass (*Equus kiang*), a quagga, (*Equus quagga*), or a Mountain zebra (*Equus zebra*). The source of donor cells may be any member of the family of equidae, including any of the above equidae and infertile equidae such as mules.

The invention is illustrated by specific examples below. It will be understood by those skilled in the art that the examples are merely illustrative and that any method for collection and preparation of donor cells, for collection and preparation of oocytes, for nuclear transfer and/or activation, for embryo transfer, and for pregnancy detection may be utilized in accordance with the invention, provided that the oocyte is activated in accordance with the method of the invention. For example, Example 5 below discloses that the oocytes were placed in an activation medium containing calcium and ionomycin. It is to be understood that the use of an ionophore, such as ionomycin, is optional and is not necessary for the method of the invention.

Further, the invention is illustrated below using a mule as a source of donor cells. This source was selected because the mule is a sterile animal, and is therefore conceived to be more difficult to reproduce than other, non-sterile members of equidae. Consequently, positive results obtained with the mule as a source of donor cells are applicable to other equidae, and results obtained with other equidae are expected to be superior to those obtained with mules.

Further, the invention is illustrated using pre-ovulatory and post-ovulatory oocytes. It is preferred to use pre-ovulatory oocytes because pre-ovulatory oocytes are obtainable by methods that are non-invasive and non-destructive to the mare. However, both pre-ovulatory and post-ovulatory oocytes are suitable for the method of the invention.

EXAMPLE 1

Donor Cells

A primary culture of fibroblast cells was established from a 45-day mule fetus recovered from a domestic horse mare using transcervical uterine lavage. Culture medium was Glasgow MEM BHK-21 supplemented with 10% FBS, 100 units/ml penicillin, and 100 µg/ml streptomycin. Incubation was performed at 38.5° C. in a humidified atmosphere of 5% $CO_2$ in air. Prior to the nuclear transfer procedure, the fibroblast cells were serum "starved" for 5 to 10 days by placing them into medium with 0.5% FBS.

EXAMPLE 2

Animals

Mares that were used as oocyte donors and as cloned-embryo recipients were of mixed breeding, 3 to 12 years old, and weighed 300 to 500 kg. The reproductive tracts of the mares were monitored by transrectal palpation and ultrasonography to assess follicular activity, ovulation, and the presence and degree of endometrial edema.

EXAMPLE 3

Oocyte Collection Procedures

Oocytes were collected by one of three methods.

1. Recent ($\leq 12$ hours) post-ovulatory oocytes (n=12) were collected by surgically excising the oviduct ipsilateral to ovulation and then flushing the oviduct in a retrograde manner with modified DPBS.

2. Pre-ovulatory oocytes (n=3) were collected by surgically excising ovaries containing a pre-ovulatory follicle ($\geq 35$ mm) approximately 30 hours after administration of 2500 IU hCG and then manually aspirating the follicle.

3. Pre-ovulatory oocytes (n=180) were collected using transvaginal aspiration (TVA) of pre-ovulatory follicles approximately 24 hours after administration of 2500 IU hCG.

EXAMPLE 4

Oocyte Handling and Culture

Oocytes collected post-ovulation were incubated for up to 6 hours in maturation medium (M-199) containing 10% FBS, 0.05 units/ml pFSH, 0.05 units/ml pLH, 10 units/ml penicillin and 10 μg/ml streptomycin. Oocytes collected pre-ovulation were incubated in maturation medium for approximately 12 hours.

EXAMPLE 5

Nuclear Transfer and Activation Procedures

Cumulus-free metaphase II oocytes and starved donor cells were placed in a manipulation drop of TL HEPES containing 7.5 μg of cytochalasin B. The first polar body and metaphase plate of the oocytes were drawn into a 25-28 ID enucleation pipette. The same pipette was used to aspirate a disaggregated donor cell nucleus and place it in the perivitelline space of an oocyte to obtain an NT couple. Fusion of NT couples was induced by a single 15 μsec, 2.2 kv/cm DC pulse in a 3.5 mm fusion chamber. Fusion medium was 3.5 M D-mannitol containing 0.5 mM HEPES and 0.05% fatty acid-free BSA. Fused NT couples were activated by placing them in an activation medium containing calcium chloride and ionomycin for 8 minutes. Three different concentrations of calcium chloride were used in the activation medium: 2 mM (n=133 oocytes), 6 mM (n=40 oocytes), and 20 mM (n=22 oocytes).

EXAMPLE 6

Embryo Transfer and Pregnancy Detection

Immediately following nuclear transfer and activation, the oocytes, hereafter referred to as embryos, were surgically transferred to the oviduct of a recipient mare (Equus caballus) that had ovulated within 24 hours prior to the transfer. One to nine embryos were transferred to each mare. Pregnancy examinations on the recipient mare were performed using transrectal ultrasonography beginning on Day 12 post-transfer.

EXAMPLE 7

Results

Seven of 195 (3.6%) cloned mule embryos were detected via transrectal ultrasonography. All of the pregnancies resulted from pre-ovulatory oocytes collected with TVA. This result is not statistically significant and is believed to be due to the fact that 180 of the 195 (92.3%) oocytes collected were by this method. Therefore, it is conceived that the method of oocyte collection and the use of pre-ovulatory or post-ovulatory oocytes is immaterial.

As shown in Table 1, the concentration of divalent calcium ions in the activation medium significantly influenced the pregnancy rate.

TABLE 1

| Calcium Concentration (mM) | Pregnancy Rate |
|---|---|
| 2 | 2/133 (1.5%) |
| 6 | 3/40 (7.5%) |
| 20 | 2/22 (9.1%) |

The data in Table 1 shows that the concentration of calcium (calcium chloride) in the activation medium significantly influenced the pregnancy rate. When the data for the two higher concentrations (6 and 20 mM) of calcium are combined, more pregnancies (P<0.05) resulted from oocytes activated in medium containing these higher levels of calcium compared to oocytes activated in medium with lower (2 mM) of calcium.

EXAMPLE 8

Ultrasonography

As shown in FIG. 1, ultrasonography showed a cloned mule conceptus at Day 32 of gestation. The embryo-proper is visible in FIG. 1, and in real-time, an embryonic heart was evident. The conceptus shown in FIG. 1 resulted from an oocyte that was activated in a medium with a calcium concentration of 6 mM, in accordance with the method of the invention.

EXAMPLE 9

Additional Data in Mules

The procedures of the above examples were repeated in order to compare results obtained with different concentrations of calcium in the activation medium and in peripheral media, that is media other than the activation medium. Oocytes from mules were placed into one of four groups as follows: In Groups 1 to 3, media was as described above in Examples 1 to 5, except for calcium concentration, which is as described below. In Group 4, media was HECM media.

Group 1—all media had a concentration of calcium of about 2 mM, referred to as 1×.

Group 2—activation medium had 3× calcium concentration, about 6 mM and peripheral media had a 1× calcium concentration.

Group 3—activation medium had 10× calcium concentration, about 20 mM and peripheral media had a 1× calcium concentration.

Group 4—activation medium had 6× calcium concentration, about 12 mM and peripheral media had a 3× calcium concentration.

The results are summarized in the Table 2.

TABLE 2

| TREATMENT | # OOCYTES | PREGNANCIES (2 weeks) |
|---|---|---|
| Group 1 (1x Ca-all media) | 115 | 2 (1.7%) |
| Group 2 (3x Ca in activation media, 1x Ca all other media) | 40 | 3 (7.5%) |
| Group 3 (10x Ca in activation media, 1x Ca all other media) | 22 | 2 (9.09%) |
| Group 4 (6x Ca in activation media, 3x Ca all other media) | 132 | 19 (14.4%) |

The data shows a significant increase in the percentage of pregnancies obtained in the oocytes activated in accordance with the method of the invention, that is in Groups 2, 3, and 4. The data further shows that increases above 3× in the activation medium produced an even higher rate of pregnancy than was obtained with 3× activation medium. Further, increasing the calcium concentration in both the activation medium and in peripheral media produced the highest percentage of pregnancies produced.

Of the above pregnancies, neither of the 2 two-week pregnancies of Group 1 was detectable at 30 days. In Group 2, 2 of the 3 two-week pregnancies were detectable at 30 days. In Group 4, 9 of 12 two-week pregnancies were detectable at 30 days. Five of these were detectable at 45 days, and 3 of these were detectable at 120 days.

EXAMPLE 10

Data in Horses

The protocol of Group 4 of Example 9 was repeated with 59 horse oocytes. Of these, pregnancy was detected at two weeks in 6 mares, 4.4%. Of these 6, 3 pregnancies were detected at 30 days and 1 was detected at 45 days.

EXAMPLE 11

Media Used in the Above Examples

Maturation Medium:
Tissue Culture Medium (TCM)—199 with Earl's salts
1.4 mM $CaCl_2$ (1×)
10% Fetal Bovine Serum (FBS)
0.05 units FSH
0.05 units LH
100 units penicillin
100 micrograms streptomycin Manipulation Medium:
PB1 (Whittingham, D G, J. Reprod. Fert., 37(1):159-162 (1974)
Dulbecco's phosphate buffered saline
1.4 mM $CaCl_2$ (1×)
0.5 mM $MgCl_2$
0.33 mM Na-pyruvate
5.56 mM Glucose
3 mg/ml Bovine Serum Albumin (BSA)—fraction 5
100 units penicillin
10 micrograms streptomycin Transfer Medium
PB1 (as in Manipulation Medium) except 0.7 mM $CaCl_2$ (1×)
Holding/Activation/Culture Medium for Group 4 in Example 9 and in horses in Example 10
HECM (Ball et al., Amer. J. Vet. Res., 54(7):1139-44 (1993)
Ham's F-12+Dulbecco's Minimum Essential Medium (DMEM)—(50:50, v:v)
0.71 mM $CaCl_2$ (1×)
29 mM $NaHCO_3$
5 micrograms/ml insulin
5 micrograms/ml transferrin
5 ng/ml Na-selenite
10 ng/ml EGF
50 IU penicillin
50 micrograms streptomycin The above data represents the first report of an establishment of a cloned equine pregnancy in vivo. Previously, only an in-vitro report of cleavage of cloned equine embryos had been reported, and none of these embryos developed beyond the 8 to 16 cell stage. Increasing the calcium concentration, as described above, is a significant breakthrough in increasing the pregnancy rate in equines, and has important implications for increasing the production of equidae by such methods as nuclear transfer and in vitro fertilization.

All articles and patents cited in this application are incorporated herein by reference.

Further modifications, uses, and applications of the invention described herein will be apparent to those skilled in the art. It is intended that such modifications be encompassed in the following claims.

The invention claimed is:

1. A method for activating an equine oocyte comprising exposing the oocyte in a medium to a concentration of divalent calcium ions of about 4 mM or higher during activation of the oocyte, and activating the oocyte.

2. The method of claim 1 wherein the exposure is during activation in an activation medium.

3. The method of claim 2 wherein an ionophore is included in the activation medium.

4. The method of claim 3 wherein the ionophore is ionomycin.

5. The method of claim 3 wherein the oocyte is incubated with cyclohexamide.

6. The method of claim 1 wherein activation is by electroporation.

7. The method of claim 1 wherein activation is by sperm.

8. The method of claim 1 wherein the equine source of the oocyte is selected from the group consisting of ass, Burchell's zebra, domestic horse, Mongolian wild horse, Asian wild ass, Grevy's zebra, wild ass, quagga, and mountain zebra.

9. The method of claim 1 wherein the equine is a mule or a domestic horse.

10. The method of claim 1 wherein the oocyte is a pre-ovulatory oocyte.

11. The method of claim 1 wherein the concentration of calcium in the medium is about 6 mM or higher.

12. The method of claim 11 wherein the concentration of calcium in the medium is about 6 mM.

13. The method of claim 11 wherein the concentration of calcium in the medium is about 12 mM.

14. The method of claim 11 wherein the concentration of calcium in the medium is about 20 mM.

15. The method of claim 1 wherein one or more of media in which oocytes are incubated prior to activation or following activation has a calcium concentration of at least 4 mM.

16. The method of claim 2 wherein one or more of media in which oocytes are incubated prior to activation or following activation has a calcium concentration of at least 4 mM.

17. A method for establishing a pregnancy in an equine comprising exposing an equine oocyte to a medium comprising calcium at a concentration of about 4 mM or more during activation of the oocyte, and activating the oocyte, thereby obtaining an embryo, and transferring the embryo into a female equine.

18. The method of claim 17 wherein the exposure is during activation in an activation medium.

19. The method of claim 17 wherein the activation is with sperm and pregnancy is established by in-vitro fertilization.

20. The method of claim 17 wherein the oocyte is enucleated and is fused with the nucleus of a donor cell.

* * * * *